United States Patent [19]

Quinn

[11] Patent Number: 6,148,059
[45] Date of Patent: Nov. 14, 2000

[54] METHODS AND APPARATUS USING FLUORESCENT EMISSIONS TO DETERMINE CONCENTRATION OF MATERIAL IN OBJECT

[75] Inventor: Alan P. Quinn, Corning, N.Y.

[73] Assignee: Corning Incorporated, Corning, N.Y.

[21] Appl. No.: 09/465,969

[22] Filed: Dec. 15, 1999

Related U.S. Application Data

[60] Provisional application No. 60/113,479, Dec. 21, 1998.

[51] Int. Cl.$^7$ ................................................. G01N 23/223
[52] U.S. Cl. ................................................. 378/46; 378/45
[58] Field of Search .................................. 378/45, 46, 48, 378/49

[56] References Cited

U.S. PATENT DOCUMENTS

| | | | |
|---|---|---|---|
| 3,621,245 | 11/1971 | Clayton et al. | 250/51.5 |
| 4,349,736 | 9/1982 | Miller | 378/83 |
| 5,027,379 | 6/1991 | Hunt et al. | 378/4 |
| 5,187,727 | 2/1993 | Vogler et al. | 378/50 |
| 5,537,451 | 7/1996 | Serebryakov et al. | 378/45 |
| 6,023,496 | 2/2000 | Kuwabara | 378/45 |

*Primary Examiner*—David P. Porta
*Assistant Examiner*—Pamela R. Hobden
*Attorney, Agent, or Firm*—Robert L. Carlson

[57] ABSTRACT

A method and apparatus determine a concentration of dopant in soot that constitutes at least a portion of a soot preform used to form an optical waveguide. The soot is irradiated with photons, X-ray fluorescent emissions from the irradiated soot are detected, and the concentration of dopant is determined based on the detected X-ray fluorescent emissions. Additionally, the concentration of dopant in layers of soot on the soot preform can be individually determined. Furthermore, the manufacture of the soot preform can be controlled by utilizing the detected X-ray fluorescent emissions to determine a deviation between a concentration of dopant in the soot and a predetermined concentration, and adjusting deposition conditions based on the deviation.

11 Claims, 5 Drawing Sheets

METHODS AND APPARATUS USING FLUORESCENT EMISSIONS TO DETERMINE CONCENTRATION OF MATERIAL IN OBJECT

This application claims the benefit of U.S. provisional Ser. No. 60/113,479 filed Dec. 21, 1998.

BACKGROUND OF THE INVENTION

1. Field of the Invention

The present invention relates to methods and apparatus using fluorescent emissions to determine a concentration of a material in an object. More specifically, the present invention relates to methods and apparatus using fluorescent emissions to determine a concentration of dopant in a soot preform used to form optical waveguide fibers ("optical fibers").

2. Description of the Related Art

An optical fiber typically includes a cladding made of pure silica ($SiO_2$) and a core made of silica doped with germania ($GeO_2$). The germania dopant alters the refractive index of the silica in the core. Portions of the core often contain different concentrations of germania, resulting in different refractive indexes along the diameter of the core. The distribution of refractive indexes along the diameter of the core (i.e., the refractive-index profile) determines operating characteristics of the optical fiber.

The optical fiber can be formed by a conventional process known as outside vapor deposition ("OVD"). Generally, the OVD process involves forming a soot preform by burning a gaseous mixture to produce soot containing silica and germania, successively depositing layers of the soot onto a mandrel to form a core portion of the soot preform, burning a gaseous mixture to produce soot containing only silica, and successively depositing layers of that soot onto the core portion to form a cladding portion of the soot preform. The soot preform is consolidated by sintering to form a glass blank. An optical fiber is drawn from the glass blank. The concentrations of germania in tie soot layers forming the core portion primarily determine the concentrations of germania along the diameter of the core of the resulting optical fiber.

If the concentrations of germania in the soot layers can be measured, a soot preform can be evaluated to determine whether it can be expected to produce an optical fiber with a desired refractive-index profile. Also, if dopant concentration can be determined on-line, i.e., during soot deposition, the dopant concentration can be monitored and altered to obtain a desired profile.

Japanese Patent Application No. 59-106803 (Hara) and U.S. Pat. No. 4,618,975 (Glantschnig) disclose techniques that use X-ray attenuation to nondestructively evaluate the concentrations of germania in soot preforms. Both approaches measure X-ray attenuation at two energies. Hara's scheme relies upon the fact that the dopant (Ge) to matrix (Si) attenuation ratio changes with X-ray photon energy. Hara's scheme is not particularly sensitive for soot preforms, however, because the ratio is nearly constant over any practical X-ray energy range. Glantschnig's method is based on the fact that the ratio of dopant attenuation (absorption) to density attenuation (scattering) changes with X-ray photon energy. Like Hara's ratio, Glantschnig's ratio is nearly constant over an energy range practical for soot preforms. Thus, Glantschnig's method confounds density changes with dopant concentration changes.

These X-ray attenuation methods have additional disadvantages. For example, if a soot preform has multiple dopants, X-ray attenuation due to one dopant cannot be distinguished from X-ray attenuation due to another dopant. Moreover, the measurement of attenuation requires precise location of the preform within the measurement apparatus, and therefore it is expensive to implement.

U.S. Pat. No. 4,292,341 (Marcuse) discloses methods of performing on-line measurements of dopant concentration in a modified chemical vapor deposition process, which does not form a soot preform but instead immediately consolidates the soot into a glass blank. One of the disclosed methods employs X-ray attenuation, which has many of the problems mentioned above. Another method measures dopant concentration by irradiating the glass blank with ultraviolet light and measuring the fluorescent emissions of the glass blank. It is believed that the latter method will not work with a soot preform, since soot is opaque to ultraviolet and visible light.

SUMMARY OF THE INVENTION

Objects and advantages of the invention may be apparent from the description that follows. Further advantages of the invention also may be learned by practice of the invention.

An aspect of the present invention includes a method of determining a concentration of dopant in soot that constitutes at least a portion of a soot preform used to form an optical waveguide. The method comprises the steps of irradiating the soot with photons, detecting X-ray fluorescent emissions from the irradiated soot, and determining the concentration of dopant based on the detected X-ray fluorescent emissions.

Another aspect of the invention includes a method of controlling the manufacture of a soot preform used to form an optical waveguide. The method comprises the steps of depositing soot on the soot preform, irradiating the soot with photons, detecting X-ray fluorescent emissions from the irradiated soot, utilizing the detected X-ray fluorescent emissions to determine a deviation between a concentration of dopant in the soot and a predetermined concentration, and depositing additional soot on the soot preform under deposition conditions adjusted based on the deviation.

Yet another aspect of the present invention includes an apparatus for determining dopant concentration in soot that constitutes at least a portion of a soot preform used to form an optical waveguide. The apparatus comprises a photon source that irradiates the soot with photons, a fluorescence sensor that detects X-ray fluorescent emissions from the irradiated soot, and a determination device that determines a concentration of dopant in the soot based on the detected X-ray fluorescent emissions.

It is to be understood that the foregoing general description and the following detailed description are exemplary and explanatory only and are not restrictive of the invention as claimed.

BRIEF DESCRIPTION OF THE DRAWINGS

The accompanying drawings illustrate embodiments of the invention and together with the description serve to explain the principles of the invention.

DETAILED DESCRIPTION OF THE PREFERRED EMBODIMENTS

Reference will now be made in detail to presently preferred embodiments of the invention. Wherever possible, the same reference numbers will be used throughout the drawings to refer to the same or like parts.

The present invention determines the concentration of a dopant in a soot preform, preferably on-line, real-time, layer-by-layer measurement of dopant concentration. More specifically, the present invention irradiates a soot preform with photons of sufficient energy to excite or ionize the dopant atoms. When the dopant atoms become sufficiently ionized, they return to their ground state by a decay process known as fluorescence. In this decay process, the dopant atoms emit photons of energy, i.e., fluorescent emissions. In general, the intensity of the fluorescent emissions will be proportional to the number of dopant atoms in the soot preform, as well as the amount of soot deposited. Accordingly, the present invention detects the fluorescent emissions and determines the concentration of dopant based on the detected fluorescent emissions.

Figure 1:
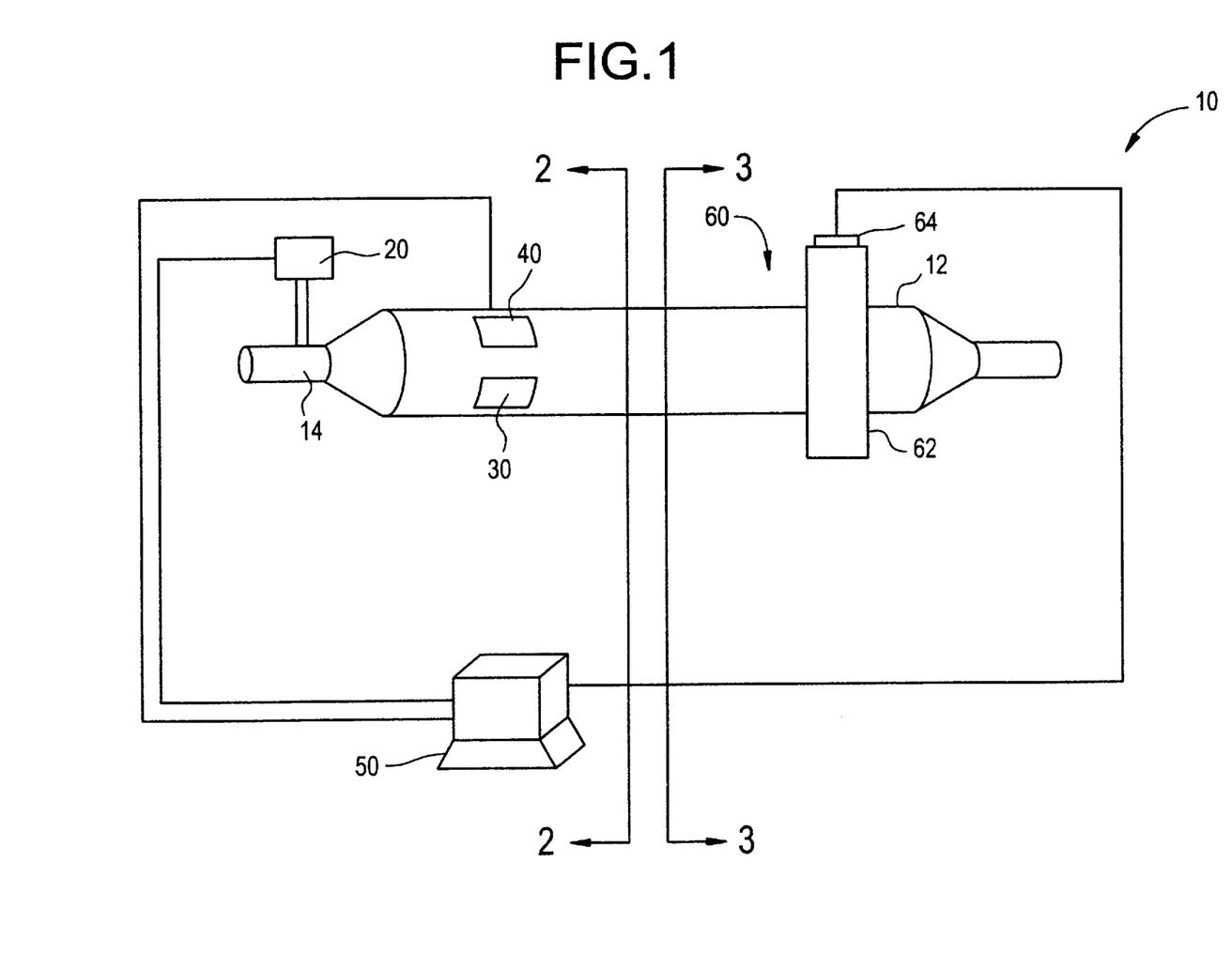
FIG. 1 is a side view of an embodiment of an apparatus according to the present invention for determining a concentration of dopant in a soot preform.
Figure 2:
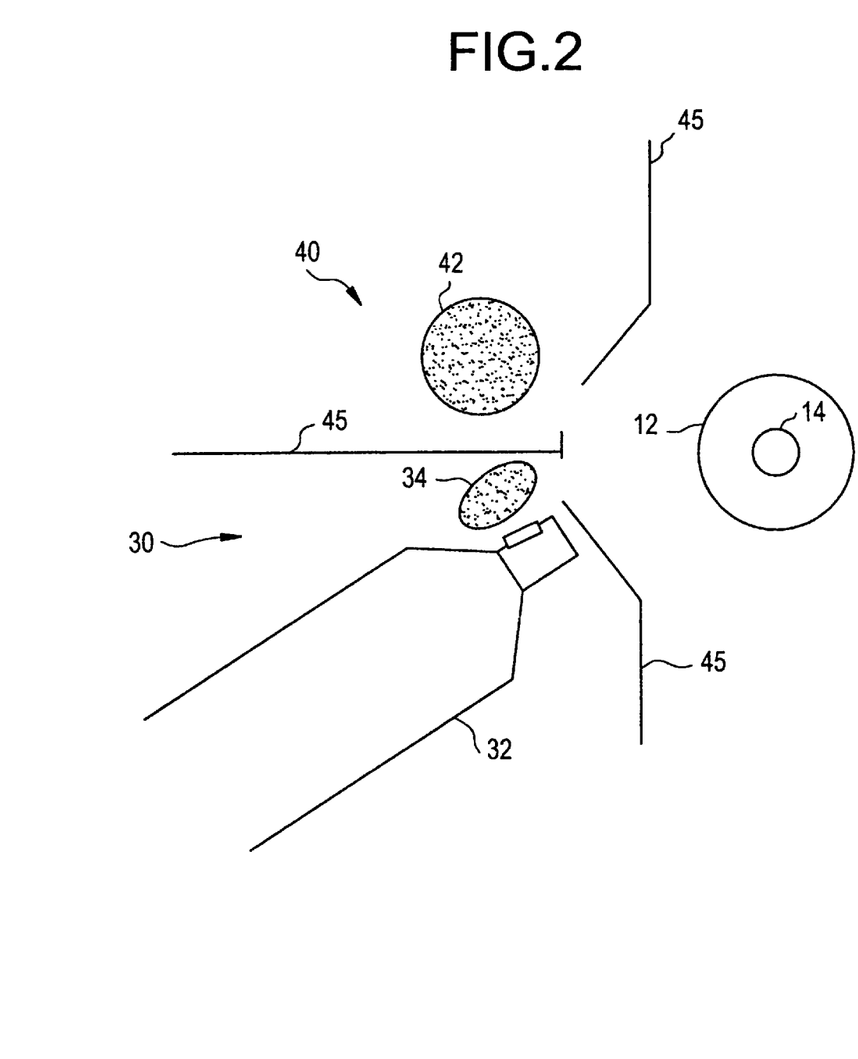
FIG. 2 is a cross-sectional view taken along line 2—2 of FIG. 1 showing a photon source and a fluorescence sensor.
Figure 3:
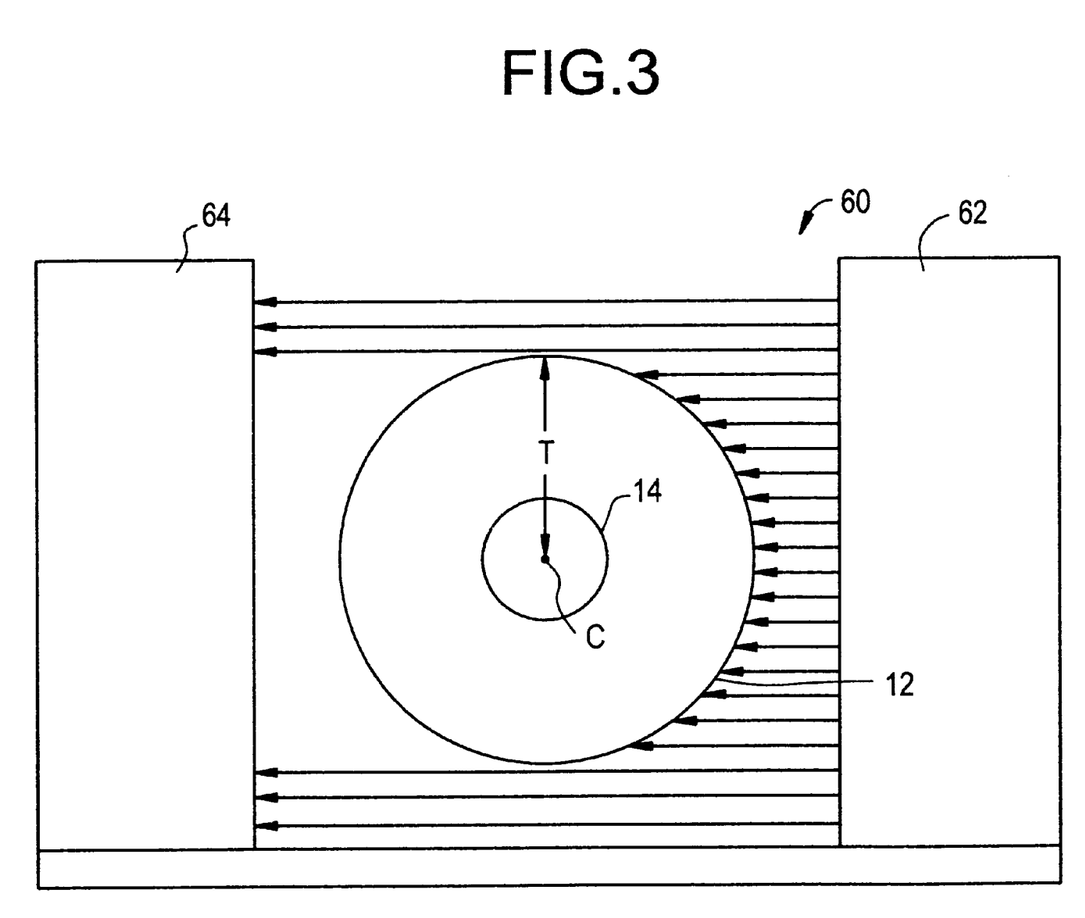
FIG. 3 is a cross-sectional view taken along line 3—3 of FIG. 1 showing a thickness-parameter measuring device.

FIGS. 1 to 3 illustrate a preferred embodiment of an apparatus 10 according to the present invention for determining the concentration of dopant in a soot preform 12 on a mandrel 14. The apparatus 10 includes a photon source 30, a fluorescence sensor 40, and a determination device 50. The apparatus can also include a thickness-parameter-measuring device 60 and a weight-measuring device 20.

The photon source 30 irradiates the soot preform 12 with photons of sufficient energy to ionize the dopant (e.g., germania) atoms. Effective photons include, for example, X rays, soft X rays, gamma rays, and extreme ultraviolet light. The photon source 30, as shown in FIG. 2, preferably includes a 200-watt, rhodium X-ray tube 32 (TruFocus Corp. TFS 6066 FGA/Rh) exciting a selenium secondary target 34 (used for GeO2/SiO2 binary soots). Different dopants can be detected using different secondary targets.

The fluorescence sensor 40 detects the intensity of the fluorescent emissions of the dopant (preferably X-ray emissions) and provides a corresponding signal to the determination device 50. Preferably, the fluorescence sensor 40 includes a detector 42 arranged on the same side of the soot preform 12 as the photon source 30, as shown in FIG. 2. The detector 42 can be, for example, a xenon filled sealed proportional counter with a single channel analyzer circuit.

The photon source 20 and the fluorescence sensor 30 preferably form a relatively simple X-ray spectrometer, including associated shielding 45. If it is desired to determine the concentrations of multiple dopants in the soot or to detect fluorescence from the mandrel 14, a more sophisticated spectrometer design will be required. The required design can be readily determined by one skilled in the art. For example, if it is desired to measure fluorescence from the mandrel 14 through $GeO_2/SiO_2$ binary soots, the emissions of the rhodium X-ray tube 32 can be scattered by epoxy for excitation, and a multichannel analyzer can be used with the xenon filled sealed proportional counter 42 to resolve mandrel fluorescence from dopant fluorescence.

The thickness-parameter-measuring device 60 measures a thickness parameter, such as the radius or diameter, of the soot preform 12. Although the thickness-parameter-measuring device 60 is shown offset to the right in FIG. 1 for ease of illustration, it preferably measures along the center portion of the soot preform 12. As shown in FIG. 3, the thickness-parameter-measuring device 60 can be a laser shadowing micrometer that includes a source 62 that emits optical beams and a detector 64 that detects optical beams emitted by the source 62. Based on the detected. Optical beams, the detector 64 provides a signal to the determination device 50. This information permits a thickness parameter of the soot preform 12 to be determined for each traverse during soot laydown. Commercially available devices that perform this function include Anritsu KL-154A and Keyence LS-5001.

The weight-measuring device 20 measures the weight of the soot preform 12 and provides a corresponding signal to the determination device 50. A preferred weight-measuring device 20 includes a resistance load cell connected to one end of the mandrel 14 upon which the soot preform 12 is formed. The other end of the mandrel 14 can be chucked to a drive motor (not shown).

Preform weight is recorded continuously during soot laydown. Variations due to preform runout are eliminated by averaging the individual load cell readings acquired during a preform rotation or an integral number of preform rotations. Variations due to preform traverse location are accomodated by synchronizing weight acquisition with preform traverse location. In other words, although weight measurements are preferably continuous, an identifier or flag is associated with the starting point of pertinent weight measurements for each traverse, and the starting point is the same in each traverse. Preform weight at a given segment is the average of these synchronized, averaged readings. Weight of a segment is the weight gain observed since the previous segment.

Preferably, the weight-measuring device 20 measures the weight of the soot preform 12 continuously during the formation of the soot preform 12. Weight of any number of soot layers can be determined.

The determination device 50 receives the signals from the fluorescence sensor 40, and in certain embodiments from the thickness-parameter-measuring device 60 and possibly also from the weight-measuring device 20, and determines a concentration of dopant in the soot preform 12. The determination device 50 can be a computer. The manner in which the determination device 50 determines the dopant concentration will be explained below in more detail with reference to the preferred photons, i.e., X rays.

For an infinitely thin layer of soot, dopant fluorescence intensity is directly proportional to incident flux, dopant concentration, and mass of soot:

$$I_D = I_P\, A\, W_D\, Wt \tag{1}$$

where $I_D$ = intensity of dopant fluorescence $I_P$=intensity of primary excitation
A=a proportionality constant
$W_D$=weight fraction (concentration) of dopant
Wt=weight of soot
or $$I_D = I_P \, A \, W_D \, \rho \, t \tag{2}$$

where
$\rho$=density of soot (grams/cm$^3$)
t=thickness of soot (cm)

For soot of many layers, fluorescence intensity from a layer is reduced when primary excitation and dopant fluorescence are attenuated by any overlaying layers. Dopant fluorescence from layer L in a specimen of N layers is $$I_{D,L} = I_P \, A \, T_{P,N,L} \, (W_D \rho t)_L \, T_{D,N,L} \tag{3}$$

where
$I_{D,L}$=intensity of dopant fluorescence from layer L
$T_{P,N,L}$=fraction of primary excitation transmitted through overlaying soot layers, i.e., layers N through (L+1)
$(W_D \, \rho \, t)_L$=concentration, density, and thickness of layer L
$T_{D,N,L}$=fraction of dopant fluorescence transmitted through overlaying soot layers, i.e., layers N through (L+1)

Total dopant fluorescence intensity is the summation of intensity from each of the N layers, $$I_D = \sum_{L=1}^{N} I_{D,L} \tag{4}$$

The fraction of X rays transmitted through a layer is given by the Beer—Lambert law:

$$T = I/I_O = \exp(-\mu \rho t) \tag{5}$$

where
T=fraction of X rays transmitted
$\mu$=mass attenuation coefficient (cm$^2$/gram)
$\rho$=density (gram/cm$^3$)
t=thickness (cm)

The mass attenuation coefficient for a compound or mixture is the mass weighted sum of attenuation coefficients of the soot components:

$$\mu = W_1 \mu_1 + W_2 \mu_2 + \ldots W_N \mu_N \tag{6}$$

where
$W_N$=weight fraction of Nth component
$\mu_N$=mass attenuation coefficient of Nth component For a GeO$_2$/SiO$_2$ "binary" soot, the mass attenuation coefficient for attenuation of Ge fluorescent radiation by the soot can be determined as follows:

$$\mu = W_{GEO2} \mu_{GEO2} + W_{SIO2} \mu_{SIO2} \tag{7}$$

where
$W_{GEO2}$=weight fraction of GeO$_2$
$\mu_{GEO2}$=mass attenuation coefficient of GeO$_2$
$W_{SIO2}$=weight fraction of SiO$_2$
$\mu_{SIO2}$=mass attenuation coefficient of SiO$_2$ Assuming stoichiometry for GeO$_2$ $$W_{GE} = (AtWt_{GE}/(AtWt_{GE} + (2 \, AtWt_O))) \, W_{GEO2} \tag{8}$$

$$W_O = (AtWt_O/(AtWt_{GE} + (2 \, AtWt_O))) \, W_{GEO2} \tag{9}$$

where
$AtWt_{GE}$=atomic weight of germanium
$AtWt_{SI}$=atomic weight of silicon
$AtWt_O$=atomic weight of oxygen Thus, $$W_{GE} = 0.695 \, W_{GEO2} \tag{10}$$

$$W_O = 0.305 \, W_{GEO2} \tag{11}$$

Similarly, assuming stoichiometry for SiO$_2$ $$W_{SI} = (AtWt_{SI}/(AtWt_{SI} + (2 \, AtWt_O))) \, W_{SIO2} \tag{12}$$

$$W_O = (AtWt_O/(AtWt_{SI} + (2 \, AtWt_O))) \, W_{SIO2} \tag{13}$$

Thus, $$W_{SI} = 0.467 \, W_{SIO2} \tag{14}$$

$$W_O = 0.533 \, W_{SIO2} \tag{15}$$

For a GeO$_2$/SiO$_2$ "binary" soot, where $$W_{GEO2} + W_{SIO2} = 1.0 \tag{16}$$

then, $$W_{GE} = 0.695 \, W_{GEO2} \tag{17}$$

$$W_{SI} = 0.467 \, W_{SIO2} \tag{18}$$

$$W_O = 0.305 \, W_{GEO2} + 0.533 \, W_{SIO2} \tag{19}$$

Each elemental weight fraction can be rewritten in terms of dopant concentration $W_{GEO2}$:

$$W_{GE} = 0.695 \, W_{GEO2} \tag{20}$$

$$W_{SI} = 0.467 \, (1.0 - W_{GEO2}) \tag{21}$$

$$W_O = 0.305 \, W_{GEO2} + 0.533 \, (1.0 - W_{GEO2}) \tag{22}$$

Finally, the soot mass attenuation coefficient $\mu$ can be expressed in terms of dopant concentration:

$$\mu = ((0.695 \, W_{GEO2}) \mu_{GE}) + \tag{23}$$
$$((0.467(1.0 - W_{GEO2})) \mu_{SI}) +$$
$$((0.305 \, W_{GEO2} + 0.533(1.0 - W_{GEO2})) \mu_O)$$

Attenuation depends not only on material composition, but also on X-ray energy. To estimate attenuation of the primary excitation X rays, select appropriate coefficient values. For attenuation of dopant emissions, other values are appropriate. A preferred embodiment employs a selenium metal secondary target providing "monochromatic" selenium K X rays at 11.2–11.7 KeV. The resultant Ge K fluorescent X rays are predominantly 9.9 KeV.

Mass attenuation coefficients have been tabulated by element and photon energy. For example, S. M. Seltzer, *Calculation of Photon Mass Energy-Transfer and Mass Energy-Absorption Coefficients,* Radiation Research, Vol. 136, 147–170 (1993), gives the following values:

|  | by Ge | by Si | by O |
| --- | --- | --- | --- |
| Ge K-alpha (9.88 KeV) | 38.7 | 35.2 | 6.2 |
| Se K-alpha (11.2 KeV) | 194. | 23.4 | 4.2 |

In summary, the fraction of X rays transmitted through any one layer can be calculated by (1) noting the X-ray photon energy; (2) noting the dopant concentration; (3) selecting elemental mass attenuation coefficient values for the photon energy of interest from published tabulations; (4) computing a material attenuation coefficient using equation (23); (5) noting density and thickness of the soot layer; and (6) computing the fraction transmitted T using equation (5).

The fraction transmitted by many layers is the product of the fractions transmitted by each of the N layers:

$$T = T_1 * T_2 \ldots * T_N \qquad (24)$$

Given the dopant concentration, density, and thickness of each soot layer, attenuation of the primary excitation X rays as they penetrate the outer soot layers to reach the Lth soot layer ($T_{P,N,L}$) can be calculated. Also, attenuation of the dopant fluorescent radiations as they penetrate the soot layers outward from the Lth layer ($T_{D,N,L}$) can be calculated.

Three preferred embodiments have been developed to determine dopant concentration on-line during soot deposition. A first embodiment determines dopant concentration using detected fluorescent emissions of the soot and on-line measurements of soot weight and thickness. A second embodiment determines dopant concentration using detected fluorescent emissions of soot and detected fluorescent emissions (preferably X-ray emissions) of the mandrel 14. A third embodiment, which can be used with an infinitely thick soot, determines dopant concentration using only detected fluorescent emissions of the soot.

Figure 4:
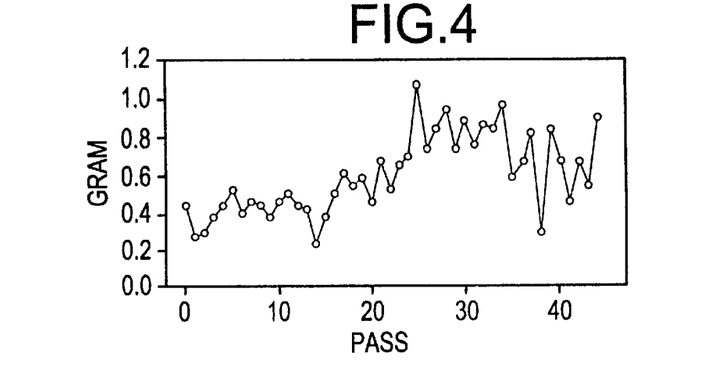
FIG. 4 is a graph showing an example of soot weights determined from measurements made by a weight-measuring device.
Figure 5:
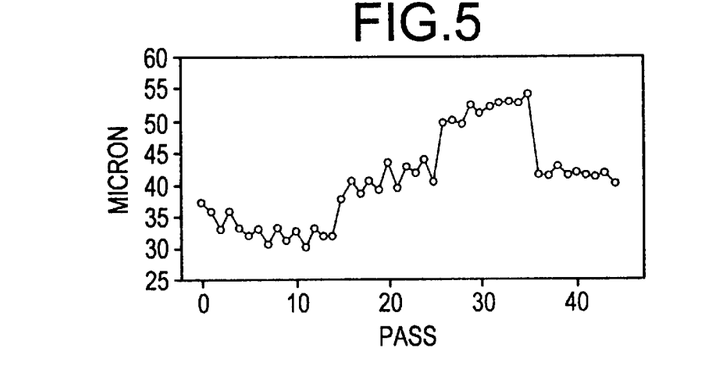
FIG. 5 is a graph showing an example of soot thicknesses determined from measurements made by the thickness-parameter measuring device.
Figure 6:
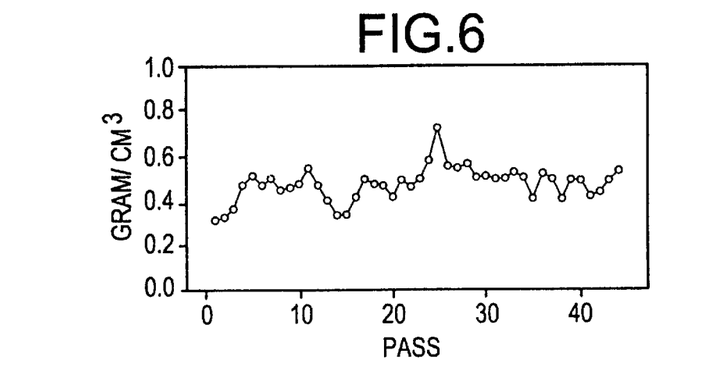
FIG. 6 is a graph showing an example of soot densities determined from the soot weights and thicknesses.

In the first preferred embodiment, the dopant X-ray fluorescence, weight, and a thickness parameter of the soot preform 12 are measured by the fluorescence sensor 30, weight-measuring device 20, and the thickness-parameter-measuring device 60, respectively, after each layer of soot is deposited on the soot preform 12. The weight Wt of each individual layer can be determined as the difference between the weight before and after depositing that layer. Similarly, the thickness t of each soot layer can be determined from the difference between the measured thickness parameter before and after depositing that layer. Thus, with a known preform traverse length, soot density ρ for each layer can be calculated. As an example, the weight data (FIG. 4) and the thickness data (FIG. 5) can be used to obtain the density data (FIG. 6).

Consequently, after the first soot layer has been deposited, values for the intensity of dopant fluorescence $I_D$, density of soot ρ, and thickness of soot t for that first soot layer are available. A value for ($I_P$ A) can be established by calibration, as explained below. The determination device 50 can then determine the dopant concentration $W_D$ in the first layer by iteratively solving equation (2). Specifically, starting with an approximation of dopant concentration $W_D$, a predicted intensity of dopant fluorescence is calculated using equation (2). After comparing the predicted intensity with the observed intensity $I_D$, the estimate of dopant concentration $W_D$ is adjusted and used to compute a new predicted intensity. When the predicted intensity and the observed intensity $I_D$ reasonably agree, the determination device 50 has determined the dopant concentration $W_D$ in the first layer.

After the second soot layer has been deposited, values for dopant X-ray fluorescence intensity $I_D$ for the two layer preform, along with the density and thickness of the second layer, are available. Assuming the dopant concentration obtained for the first layer is correct, equation (4) is invoked and choice of dopant concentration of the second layer refined until dopant fluorescence intensity predicted for the two layer preform reasonably matches the observed. This scheme repeats with each soot layer.

In the second preferred embodiment, the preform mandrel can be caused to fluoresce, and the mandrel fluorescence observed when layers of soot are deposited. The dopant X-ray fluorescence and the mandrel fluorescence are measured by the fluorescence sensor 30 each time a layer of soot is deposited on the soot preform 12.

A zirconia ($ZrO_2$) mandrel is preferably used. When excited by rhodium K X rays (20.1 KeV) from the photon source 30, the mandrel 14 will emit Zr K X rays at 15.7 KeV. The Zr mandrel intensity decreases after deposition of each soot layer. The intensity decrease is related to the amount and composition of the overlaying soot layers, that is, to the layer densities, layer thicknesses, and dopant concentrations. This embodiment does not require measurement of either preform weight or preform diameter.

The mandrel intensity observed through a soot preform of N layers is given by $$I_M = I_P \, B \, T_{P,N} \, T_{F,N} \qquad (25)$$

where $I_M$=intensity of mandrel fluorescence $I_P$=intensity of primary X rays exciting the mandrel B=a proportionality constant $T_{P,N}$=fraction of primary X rays transmitted through N layers of soot $T_{F,N}$=fraction of mandrel fluorescent X rays transmitted through N layers of soot $T_{P,N}$ and $T_{F,N}$ are to be evaluated as in equation (24), above.

There are now two simultaneous equations, one for dopant fluorescence (4) and one for mandrel fluorescence (25). There are two unknowns. The first unknown is dopant concentration $W_D$, which appears directly in the dopant fluorescence equation and in the fraction transmitted T terms of both equations. The second unknown is the product of density ρ times thickness t, that is, the mass per unit area in grams/cm². ($I_P$ A) and ($I_P$ B) are established by calibration (as explained below). As above, the two equations can be solved simultaneously by iteration.

Figure 7:
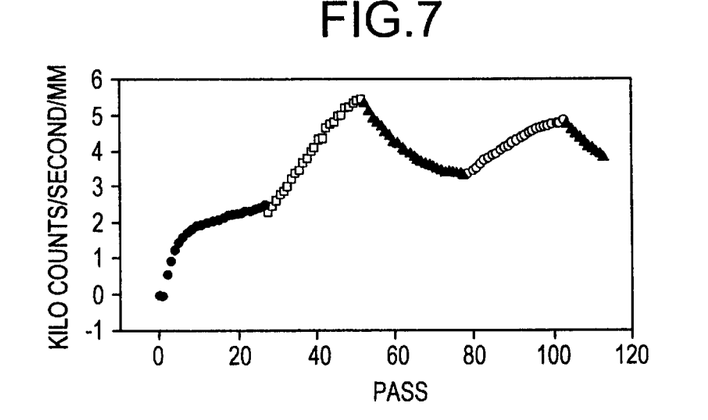
FIG. 7 is a graph showing an example of measurements of dopant fluorescence intensity.
Figure 8:
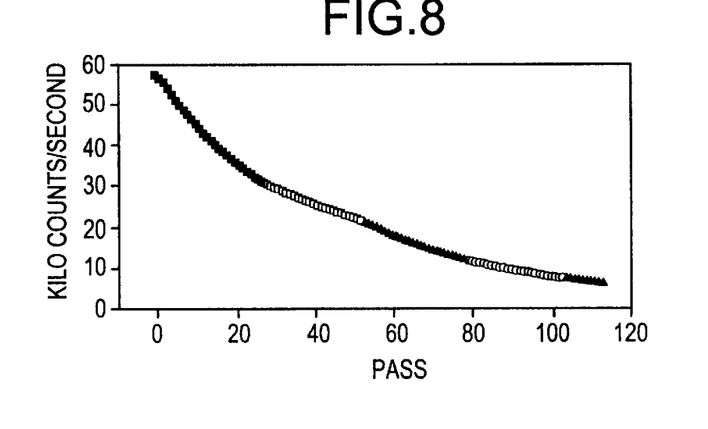
FIG. 8 is a graph showing an example of measurements of mandrel fluorescence intensity.

FIGS. 7 and 8 show dopant and mandrel X-ray emission intensity, respectively, measured during a CVD soot deposition experiment consisting of a sequence of five (5) segments. Process parameters such as oxygen flow rate, reactant flow rate, and fuel to air ratio were varied between segments, but held constant within each segment. The process parameters for the third and fifth segments were identical.

It can be seen from FIGS. 7 and 8 that many soot layers contribute to the X-ray emission counts being collected. Thus, for example, as illustrated in FIG. 7, the first experimental segment exhibited an exponential progression of X-ray emission counts, but as more layers were deposited using the first experimental process conditions, the X-ray emission counts/pass settled into a linear relationship. Also, as illustrated in FIG. 8, the X-ray emission intensity of the mandrel continuously decreased as more layers of soot were deposited, but the amount of decrease depended on the process parameters employed to deposit the soot. Because underlying layers can have an impact on subsequent layers, and because the degree with which these underlying layers have an effect changes as more layers are deposited, one would think that it would be difficult to obtain useful information as to individual layers of soot being deposited.

Figure 9:
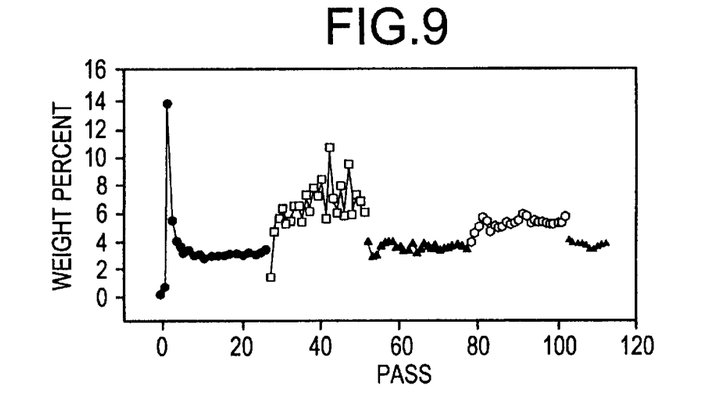
FIG. 9 is a graph showing an example of predicted dopant concentration.

However, as illustrated in FIG. 9, using the techniques of the present invention described herein, the X-ray emission data obtained can be used to obtain very useful information. FIG. 9 illustrates dopant concentration as determined by simultaneous solution of the dopant and mandrel fluorescence equations. Note that, when dopant weight percept is calculated as described herein, the effect of underlying layers and mandrel contribution has been accounted for. That is, dopant concentration/pass is displayed in a more linear relationship than was intensity/pass in FIGS. 7 and 8, resulting in more realistic and useful information about each dopant deposition pass. Thus, as can be clearly seen in FIG. 9, the second experiment segment gave increased dopant concentration, yet suffered from increased dopant concentration variability. Also, note that the third and fifth process conditions, which were identical, resulted in nearly identical dopant/pass curves.

The third preferred embodiment applies to "infinitely thick," homogeneous soot preforms. Infinite thickness is defined as that thickness from which 99.9% of the fluorescence intensity emanates. Radiations from greater depths are fully absorbed. Infinite thickness for a 10 weight % $GeO_2$/90 weight % $SiO_2$ soot with density of 0.5 grams/cm$^3$ is, for example, less than 1.0 millimeter. This embodiment would be accurate for such soot preforms where the outermost 1.0 millimeter thickness was homogeneous.

In this third preferred embodiment, only the dopant X-ray fluorescence $I_D$ is measured by the fluorescence sensor 30. The fluorescent intensity is $$I_D = I_P \, C \, \exp(-\mu_P) \, W_D \, \exp(-\mu_F) \qquad (26)$$

where
$I_D$=dopant fluorescence intensity
$I_P$=primary excitation intensity
C=a proportionality constant
$\mu_P$=mass attenuation coefficient for primary excitation by soot
$\mu_F$=mass attenuation coefficient for dopant fluorescence by soot
$W_D$=weight fraction (concentration) of dopant The ($I_P$ C) product is established by calibration, as explained below. The mass attenuation coefficients are calculated by equation (23). This equation can be solved iteratively for dopant concentration $W_D$, which appears directly and in $\mu_P$ and $\mu_F$.

To implement the foregoing equations, neither the source intensity $I_P$, nor the proportionality constants A, B, C need be known. Rather, the products ($I_P$ A), ($I_P$ B), ($I_P$ C) are needed. Best values are determined by calibration. For example, a set of thick, homogeneous soot preforms can be prepared over a range of dopant concentrations. These preforms can be measured according to the three preferred embodiments described above. The preforms can be sampled and analyzed independently for dopant concentration by inductively coupled plasma emission spectrometry. Then for each preferred embodiment, values are sought for ($I_P$ A), ($I_P$ B), or ($I_P$ C) that yield the best agreement of predicted and known dopant concentrations. This can be done iteratively, by refining choice of values to achieve agreement. Each embodiment has distinct values.

The present invention permits dopant concentration to be measured on-line. Among other things, on-line measurement allows the measured dopant concentration to be compared to a predetermined concentration so that soot deposition conditions can be adjusted on-line based on deviations between the measured and predetermined concentrations. For example, since soot often is deposited by burning a gaseous mixture containing silica and a dopant, such as $GeO_2$, the ratio of silica to dopant in the gaseous mixture can be adjusted based on the deviation to obtain a desired refractive-index profile.

It will be apparent to those skilled in the art that various modifications and variations can be made in the disclosed embodiments of the present invention without departing from the scope or spirit of the invention.

For example, monochromatic X-ray excitation sources, specifically secondary targets, have been considered. Polychromatic (tube) sources are also appropriate. The equations described above would then be modified to integrate (sum) across energy. This requires characterizing the source output over energy and evaluating mass attenuation coefficients over energy.

As another example, in the X-ray spectrometer design, the area of soot that is illuminated is small. That is, the fluorescent intensities are unaffected by preform size. The equations given herein are appropriate. In an alternative X-ray spectrometer design, the entire preform cross section can be viewed. Thus, the dopant fluorescence intensity increases with preform size. In fact, intensity happens to scale precisely with preform diameter. To accommodate this, a ratio of intensity to diameter can be employed, which is independent of preform diameter. For this variation, the foregoing equations should be modified to use the diameter scaled intensity rather than the raw intensity.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining a concentration of dopant in soot that constitutes at least a portion of a soot preform used to form an optical waveguide, the method comprising the steps of:

irradiating the soot with photons;

detecting X-ray fluorescent emissions from the irradiated soot; and determining the concentration of dopant based on the detected X-ray fluorescent emissions.

2. The method of claim 1, wherein the dopant includes germania, the step of irradiating includes irradiating with photons that cause germania to fluoresce, and the step of detecting includes detecting X-ray fluorescent emissions of germania.

3. The method of claim 1, further comprising the steps of:

depositing additional soot;

irradiating at least the additional soot with photons;

detecting X-ray fluorescent emissions from at least the irradiated additional soot; and determining a concentration of dopant in at least the additional soot based on the detected X-ray fluorescent emissions.

4. The method of claim 1, further comprising the step of determining a thickness parameter and weight of the soot, wherein the concentration of dopant is determined based on the detected X-ray fluorescent emissions and the determined thickness parameter and weight.

5. The method of claim 1, further comprising the step of determining an attenuation characteristic of the soot by measuring attenuation of emissions from a mandrel on which the soot is deposited, wherein the concentration of dopant is determined based on the detected X-ray fluorescent emissions and the determined attenuation characteristic.

6. A method of controlling the manufacture of a soot preform used to form an optical waveguide, the method comprising the steps of:

depositing soot on the soot preform;

irradiating the soot with photons;

detecting X-ray fluorescent emissions from the irradiated soot;

utilizing the detected X-ray fluorescent emissions to determine a deviation between a concentration of dopant in the soot and a predetermined concentration; and depositing additional soot on the soot preform under deposition conditions adjusted based on the deviation.

7. The method of claim 6, wherein the soot is deposited by burning a gaseous mixture containing silica and a dopant, and the step of depositing additional soot includes adjusting a ratio of silica to dopant in the gaseous mixture based on the deviation.

8. An apparatus for determining dopant concentration in soot that constitutes at least a portion of a soot preform used to form an optical waveguide, the apparatus comprising:

a photon source that irradiates the soot with photons;

a fluorescence sensor that detects X-ray fluorescent emissions from the irradiated soot; and a determination device that determines a concentration of dopant in the soot based on the detected X-ray fluorescent emissions.

9. The apparatus of claim 8, wherein the photon source emits photons that cause germania to fluoresce, and the fluorescence sensor detects X-ray fluorescent emissions of germania.

10. The apparatus of claim 8, further comprising a thickness-parameter-measuring device that measures a thickness parameter of the soot preform and a weight-measuring device that measures the weight of the soot, wherein the determination device determines the dopant concentration based on the detected X-ray fluorescent emissions and the measured thickness parameter and weight.

11. The apparatus of claim 8, wherein the fluorescence sensor detects X-ray fluorescent emissions from a mandrel on which the soot is deposited and the determination device determines an attenuation characteristic of the soot based on the detected X-ray fluorescent emissions from the mandrel, wherein the determination device determines the concentration of dopant based on the detected X-ray fluorescent emissions and the determined attenuation characteristic.

* * * * *